United States Patent
Guilford et al.

(10) Patent No.: US 7,776,896 B2
(45) Date of Patent: Aug. 17, 2010

(54) 5-CYANO-PROSTACYCLIN DERIVATIVES AS AGENTS FOR THE TREATMENT OF INFLUENZA A VIRAL INFECTION

(75) Inventors: William Guilford, Belmont, CA (US); Werner Skuballa, Berlin (DE); Daryl H. Faulds, Mill Valley, CA (US); Monica Kochanny, Benicia, CA (US); Wheeseong Lee, Orinda, CA (US); Bernd Radüchel, Berlin (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 12/079,602

(22) Filed: Mar. 27, 2008

(65) Prior Publication Data

US 2008/0242714 A1   Oct. 2, 2008

Related U.S. Application Data

(60) Provisional application No. 60/908,512, filed on Mar. 28, 2007.

(51) Int. Cl.
*A61K 31/41* (2006.01)
(52) U.S. Cl. .................. 514/382; 549/312; 514/470; 548/252
(58) Field of Classification Search .............. 514/382, 514/470; 549/312; 548/252
See application file for complete search history.

(56) References Cited

U.S. PATENT DOCUMENTS

| | | | |
|---|---|---|---|
| 4,219,479 A | 8/1980 | Vorbruggen et al. | |
| 4,364,951 A | 12/1982 | Skuballa et al. | |
| 4,468,395 A * | 8/1984 | VorbruHelmut et al. | 514/183 |
| 4,894,391 A * | 1/1990 | Skuballa et al. | 514/452 |
| 5,049,582 A | 9/1991 | Adler et al. | |
| 2008/0021099 A1 | 1/2008 | Faulds et al. | |

OTHER PUBLICATIONS

Vippagunta et al, "Crystalline Solids", Advanced Drug Delivery Reviews, vol. 48, pp. 3-26 (2001).*
Gavezzotti, "Are Crystal Structures Predictable?", Accounts of Chemical Research, vol. 27, pp. 309-314 (1994).*
Wolff, Manfred E. "Burger's Medicinal Chemistry, 5ed, Part I", John Wiley & Sons, 1995, pp. 975-977).*
Banker et al, "Modern Pharmaceutics, 3ed.", Marcel Dekker, New York, 1996, pp. 451 and 596.*
Extended European Search Report (search report & search opinion) for Appln. No. 07090056.8—1211 (the EP counterpart to the present US application), Jun. 22, 2007.

* cited by examiner

*Primary Examiner*—Kamal A Saeed
*Assistant Examiner*—Valerie Rodriguez-Garcia
(74) *Attorney, Agent, or Firm*—Jacqueline S. Larson

(57) ABSTRACT

This invention is directed to compounds of formula (I):

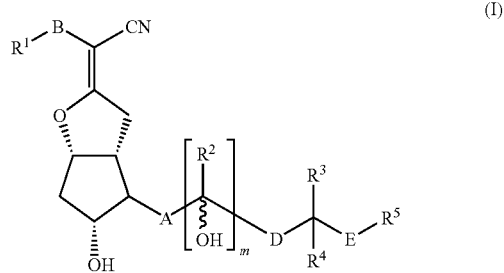

where A, B, D, E, m, and $R^1$-$R^5$ are as described herein, as single stereoisomers or as mixtures of stereoisomers, or pharmaceutically acceptable salts, clathrates, or prodrugs thereof, which compounds are useful in treating respiratory diseases associated with influenza A viruses, such as for example H5N1 and its mutations. Pharmaceutical compositions comprising the compounds of the invention and methods of preparing the compounds of the invention are also disclosed.

**

5-CYANO-PROSTACYCLIN DERIVATIVES AS AGENTS FOR THE TREATMENT OF INFLUENZA A VIRAL INFECTION

This application claims the benefit of U.S. Provisional patent application Ser. No. 60/908,512, filed on Mar. 28, 2007.

The present invention is directed to novel 5-cyano-prostacyclin derivatives and to their use in the treatment of respiratory diseases associated with influenza A viruses, such as for example H5N1 and its mutations.

BACKGROUND OF THE INVENTION

The effects of prostaglandins are mediated by their G protein-coupled receptors which are located on the cell surface. Prostaglandin $E_2$ ($PGE_2$) is of particular interest, having a wide variety of cellular effects through binding to functionally different receptor subtypes, namely the EP1, EP2, EP3 and EP4 receptors, all of which respond to $PGE_2$ but differ in their actions.

Dendritic cells (DC) are the most potent antigen-presenting cells of the immune system. Cytokine production by mature antigen-carrying DC within lymph nodes is strongly influenced by $PGE_2$ during their activation in peripheral tissues. Inflammatory cytokines such as IL-1β and TNF-α activate antigen-carrying DC to secrete IL-12 and promote the development of T-helper type 1 (Th-1) cytokine expression-biased cells. In contrast, DC activated in the presence of $PGE_2$ show impaired IL-12 production and promote the development of T-helper type 2 (Th-2) cytokine expression-biased cells [Hilkens C M et al., *J. Immunol.* 156:1722-27 (1996)]. The difference in the ability to produce IL-12 in response to $PGE_2$, established during DC activation in the peripheral tissues, is stable to the removal of cytokines and $PGE_2$.

Increased production of cytokines triggers inflammation, a normal response by the body to help fight a virus. However, when cytokine production becomes prolonged or excessive it can inflame airways, making it hard to breathe, which in turn can result in pneumonia and acute respiratory distress; and it can injure other organs, which can result in severe life-threatening complications.

It has recently been demonstrated that influenza A subtype $H5N_1$ viruses associated with the recent outbreaks of avian flu in Asia are more potent inducers of inflammatory cytokines and chemokines in primary human alveolar and bronchial epithelial cells in vitro in comparison to the more common, less virulent human flu virus H1N1. Levels of cytokines and chemokines were from 3 times to more than 10 times higher in the human cells infected with the H5N1 virus than those infected with H1N1 (N C W Chan, et al. *Respiratory Research* 2005, 6:135; article URL: http://respiratory-research.com/content/6/1/135).

These test data correlate with the high levels of cytokines and chemokines seen in patients afflicted with the avian flu, indicating that the hyper-induction of cytokines and/or chemokines is likely relevant to the pathogenesis of human H5N1 disease. Standard steroid anti-inflammatory therapy against avian flu has been of little therapeutic value. Tamiflu® has shown efficacy in that mice infected with H5N1 influenza virus survived when treated. For cases of human infection with H5N1, Tamiflu® may improve prospects for survival but clinical data are limited. Concerns have been recently raised about the safety of Tamiflu® treatment to patients having the avian flu.

It would therefore be desirable to have a therapeutic agent that inhibits the release of overstimulated cytokines and chemokines, especially TNFα interferon gamma (IFN-γ) and Interferon gamma. It would also be desirable to have a therapeutic agent that would treat diseases associated with human H5N1 and other influenza A subtype viruses while being well-tolerated by the patients.

SUMMARY OF THE INVENTION

The present invention is directed to compounds, as single stereoisomers or as mixtures of stereoisomers, or pharmaceutically acceptable salts, solvates, polymorphs, clathrates, or prodrugs thereof, that are useful as pharmaceutical therapeutic agents for the treatment of human respiratory diseases associated with influenza A viruses, such as for example H5N1 and its mutations. The compounds of the invention are more stable and exhibit a good PK profile.

Accordingly, in one aspect, the invention provides compounds of formula (I), or a pharmaceutically acceptable salt, prodrug, or clathrate thereof:

(I)

wherein,
m is zero or 1;
$R^1$ is —CH(OH)—CH$_2$(OH) or heteroaryl;
B is alkylene of 1-10 carbon atoms;
A is —CH$_2$—CH$_2$—, —CH=CH—, or —C≡C—;
$R^2$ is hydrogen or —CH$_3$;
D is a direct bond, alkylene of 1-5 carbon atoms, alkenylene of 2-5 carbon atoms or alkynylene of 2-5 carbon atoms;
$R^3$ is hydrogen, hydroxy or alkyl of 1-3 carbon atoms;
$R^4$ is hydrogen or alkyl of 1-3 carbon atoms;
or, $R^3$ and $R^4$ taken together with the carbon to which both $R^3$ and $R^4$ are attached form a cycloalkylene group of 3-6 carbon atoms;
E is —O—, —S— or a direct bond; and
$R^5$ is alkyl, alkenyl, alkynyl, cycloalkyl, heterocyclyl or optionally substituted aryl;
as a single stereoisomer or mixtures of stereoisomers.

In another aspect, this invention provides pharmaceutical compositions, which composition comprises a therapeutically effective amount of a compound of formula (I) as described herein, and a pharmaceutically acceptable excipient.

In another aspect, this invention provides a method of treating viral infections, such as influenza A viruses, in a mammal, which method comprises administering to a mammal in need thereof a therapeutically effective amount of a compound of formula (I) as described herein.

In a further aspect, the invention is directed to a method of inhibiting the release of cytokines and/or chemokines in response to infection by influenza A viruses and, in a preferred embodiment, by the influenza A subtype H5N1 virus, which method comprises administering to a mammal in need thereof a therapeutically effective amount of a compound of formula (I) as described herein. Such inhibition can be determined by one of skill in the art by methods known in the art or as taught herein, without undue experimentation.

DESCRIPTION OF THE INVENTION

Definitions

"Alkyl" refers to a straight or branched hydrocarbon chain radical consisting solely of carbon and hydrogen atoms, containing no unsaturation, having from one to ten carbon atoms, preferably one to six carbon atoms, and which is attached to the rest of the molecule by a single bond. The alkyl group may be substituted by aryl. Suitable alkyl groups include, for example, methyl, ethyl, n-propyl, 1-methylethyl (isopropyl), n-butyl, n-pentyl, 1,1-dimethylethyl (t-butyl), 3-methylhexyl, 2-methylhexyl, benzyl, p-chlorobenzyl, and the like.

"Alkenyl" refers to a straight or branched hydrocarbon chain radical consisting solely of carbon and hydrogen atoms, containing one or more double bonds, having from two to ten carbon atoms, preferably two to six carbon atoms, and which is attached to the rest of the molecule by a single bond.

"Alkynyl" refers to a straight or branched hydrocarbon chain radical consisting solely of carbon and hydrogen atoms, containing one or more triple bonds, having from two to ten carbon atoms, preferably two to six carbon atoms, and which is attached to the rest of the molecule by a single bond.

"Alkylene" refers to a straight or branched divalent hydrocarbon chain linking the rest of the molecule to a radical group, consisting solely of carbon and hydrogen, containing no unsaturation and having from one to ten carbon atoms; for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon in the alkylene chain or through any two carbons within the chain.

"Alkenylene" refers to a straight or branched divalent hydrocarbon chain linking the rest of the molecule to a radical group, consisting solely of carbon and hydrogen, containing one or more double bonds and having from two to ten carbon atoms. The alkenylene chain is attached to the rest of the molecule through a single bond and to the radical group through a single bond. The points of attachment of the alkenylene chain to the rest of the molecule and to the radical group can be through one carbon in the alkenylene chain or through any two carbons within the chain.

"Alkynylene" refers to a straight or branched divalent hydrocarbon chain linking the rest of the molecule to a radical group, consisting solely of carbon and hydrogen, containing one or more triple bonds and having from two to ten carbon atoms. The alkynylene chain is attached to the rest of the molecule through a single bond and to the radical group through a single bond. The points of attachment of the alkynylene chain to the rest of the molecule and to the radical group can be through one carbon in the alkynylene chain or through any two carbons within the chain.

"Alkoxy" refers to a radical of the formula —$OR_a$ where $R_a$ is an alkyl radical as defined above containing one to twelve carbon atoms.

"Aryl" refers to aromatic monocyclic or multicyclic hydrocarbon ring system consisting only of hydrogen and carbon and containing from 6 to 19 carbon atoms, where the ring system may be partially or fully saturated. Aryl groups include, but are not limited to, groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents independently selected from alkyl, alkoxy, halo, haloalkyl, cyano, nitro, hydroxy, carboxy, aryl, aralkyl, cycloalkyl, cycloalkylalkyl, heterocyclyl, heterocyclylalkyl, heteroaryl, and heteroarylalkyl.

"Aralkyl" refers to a radical of the formula —$R_aR_b$ where $R_a$ is an alkylene chain as defined above and $R_b$ is one or more aryl radicals as defined above; for example, benzyl, diphenylmethyl and the like.

"Clathrates" as used herein refers to substances which fix gases, liquids or compounds as inclusion complexes so that the complex may be handled in solid form and the included constituent (or "guest" molecule) subsequently releases by the action of a solvent or by melting. The term "clathrate" is used interchangeably herein with the phrase "inclusion molecule" or with the phrase "inclusion complex". Clathrates used in the instant invention are prepared from cyclodextrins. Cyclodextrins are widely known as having the ability to form clathrates (i.e., inclusion compounds) with a variety of molecules. See, for example, Inclusion Compounds, edited by J. L. Atwood, J. E. D. Davies, and D. D. MacNicol, London, Orlando, Academic Press, 1984; Goldberg, I., "The Significance of Molecular Type, Shape and Complementarity in Clathrate Inclusion", *Topics in Current Chemistry* (1988), Vol. 149, pp. 2-44; Weber, E. et al., "Functional Group Assisted Clathrate Formation—Scissor-Like and Roof-Shaped Host Molecules", *Topics in Current Chemistry* (1988), Vol. 149, pp. 45-135; and MacNicol, D. D. et al., "Clathrates and Molecular Inclusion Phenomena", *Chemical Society Reviews* (1978), Vol. 7, No. 1, pp. 65-87. Conversion into cyclodextrin clathrates is known to increase the stability and solubility of certain compounds, thereby facilitating their use as pharmaceutical agents. See, for example, Saenger, W., "Cyclodextrin Inclusion Compounds in Research and Industry", *Angew. Chem. Int. Ed. Engl.* (1980), Vol. 19, pp. 344-362; U.S. Pat. No. 4,886,788 (Schering A G); U.S. Pat. No. 6,355,627 (Takasago); U.S. Pat. No. 6,288,119 (Ono Pharmaceuticals); U.S. Pat. No. 6,110,969 (Ono Pharmaceuticals); U.S. Pat. No. 6,235,780 (Ono Pharmaceuticals); U.S. Pat. No. 6,262,293 (Ono Pharmaceuticals); U.S. Pat. No. 6,225,347 (Ono Pharmaceuticals); and U.S. Pat. No. 4,935,446 (Ono Pharmaceuticals).

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantine, norbornane, decalinyl, 7,7-dimethylbicyclo[2.2.1]heptanyl, and the like.

"Cycloalkylene" refers to a divalent saturated or partially unsaturated monocyclic ring consisting solely of carbon and hydrogen atoms and having from three to six ring carbon atoms.

"Cycloalkylalkyl" refers to a radical of the formula —$R_aR_e$ where $R_a$ is an alkylene chain as defined above and $R_e$ is a cycloalkyl radical as defined above.

"Halo" refers to bromo, chloro, fluoro or iodo.

"Haloalkyl" refers to an alkyl radical, as defined above, that is substituted by one or more halo groups, as defined above, for example, trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Heteroaryl" refers to a 3- to 18-membered fully or partially aromatic ring radical which consists of one to seventeen carbon atoms and from one to six heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, acridinyl, benzimidazolyl, benzindolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, phenazinyl, phenothiazinyl, phenoxazinyl, phthalazinyl, pteridinyl, purinyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

"Heteroarylalkyl" refers to a radical of the formula —$R_aR_g$ where $R_a$ is an alkylene chain as defined above and $R_g$ is a heteroaryl radical as defined above.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, azepinyl, 2,5-diazabicyclo[2.2.1]heptan-2-yl, hexahydro-1H-1,4-diazepinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxiranyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

"Heterocyclylalkyl" refers to a radical of the formula —$R_aR_f$ where $R_a$ is an alkylene chain as defined above and $R_f$ is a heterocyclyl radical as defined above, and if the heterocyclyl is a nitrogen-containing heterocyclyl, the heterocyclyl may be attached to the alkyl radical at the nitrogen atom. The alkylene chain may be optionally substituted as defined above for an alkyl group.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domestic animals, such as cats, dogs, swine, cattle, sheep, goats, horses, rabbits, and the like. Preferably, for purposes of this invention, the mammal is a human.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like. Preferably, a pharmaceutically acceptable acid addition salt of the invention is formed from trifluoroacetic acid or hydrochloric acid.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

A "pharmaceutical composition" refers to a formulation of a compound of the invention and a medium generally accepted in the art for the delivery of the biologically active compound to mammals, for example, humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a disease or condition of interest in the mammal, preferably a human. The amount of a compound of the invention which constitutes a "therapeutically effective amount" will vary depending on the compound, the disease or condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) stabilizing the disease or condition.

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as HPLC using a chiral column. When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

Pharmaceutical Compositions of the Invention and Administration

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, welting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 10% by weight of the compound prior to dilution of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease or condition; and the subject undergoing therapy. The effective amount can be determined by methods known to those of skill in the art. The daily dose is generally about 0.1-200 µg/kg/day, preferably about 0.5-10 µg/kg/day, when administered to human patients, it being possible for the dose to be given as a single dose to be administered once or divided into two or more daily doses.

Compounds of the invention, or pharmaceutically acceptable derivatives thereof, may also be administered simultaneously with, prior to, or after administration of one or more other therapeutic agents. They may be delivered as a co-treatment together with other anti-viral or anti-inflammatory compounds, such as, but not limited to, oseltamivir (Tamiflu™) and zanamivir (Relenza™). The compounds may be delivered to the patient at the same time or sequentially as separate formulations, or they may be combined and delivered as a single formulation. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Utility of the Compounds of the Invention

The 5-cyano-prostacyclin derivatives of the invention possess the pharmacological properties typical for prostaglandins, such as, for example, inhibition of gastric acid secretion, tracheal relaxation, and the like.

Moreover, they are distinguished over natural prostaglandins and previously known analogs thereof by an improved specificity, longer period of effectiveness and higher stability. Prior prostacyclin analogs are subject to rapid degradation, whereas the compounds of the invention exhibit an improved pharmacokinetic (PK) profile.

It has now been found that the above-described 5-cyano-prostacyclin derivatives inhibit the release of Th-1 cytokines while sparing the expression of Th-2 cytokines and enhance a polarization of T cells recruitment towards the Th-2 response and away from the Th-1 response. This makes them desirable as pharmaceuticals for treating viral diseases. More particularly, the compounds of formula (I) are useful in treating diseases associated with influenza A virus, and especially with the influenza A subtype H5N1 virus.

EMBODIMENTS OF THE INVENTION

Of the various aspects of the invention disclosed above in the Summary of the Invention, one embodiment are the compounds of formula (I) wherein $R^1$ is a monocyclic heteroaryl. In another embodiment of the compounds of the invention, $R^1$ is tetrazolyl.

Another embodiment of the compounds of the invention of formula (I) are those compounds wherein $R^1$ is —CH(OH)—CH$_2$(OH).

Another embodiment of the compounds of the invention of formula (I) are those wherein A is —CH=CH—. In a further embodiment, A is cis-CH=CH— or trans-CH=CH—.

A further embodiment of the compounds of the invention of formula (I) are those where m is 1.

Another embodiment of the invention are compounds of formula (I) where $R^2$ is hydrogen.

Another embodiment of the compounds of the invention are those of formula (I) wherein $R^3$ is hydrogen, hydroxy or $C_{1-3}$alkyl; and $R^4$ is hydrogen or $C_{1-3}$alkyl.

A further embodiment of the compounds of the invention of formula (I) are those wherein $R^3$ and $R^4$ taken together with the carbon to which both $R^3$ and $R^4$ are attached form a $C_{3-6}$cycloalkylene group.

Another embodiment of the compounds of the invention are those of formula (I) wherein $R^5$ is alkyl, cycloalkyl or aryl. A further embodiment of the compounds of the invention are those where $R^5$ is alkyl.

Further, examples of the side chain portion of the compounds of formula (I) include, but are not limited to, the following:

-continued

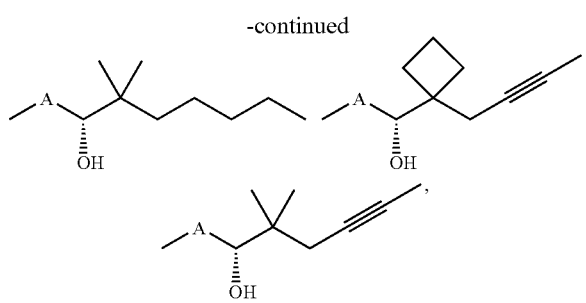

as well as structures corresponding thereto but containing some saturation in the carbon-carbon chains.

Of the various aspects of the invention disclosed above in the Summary of the Invention, another embodiment are methods of treating autoimmune diseases in a mammal, which methods comprise administering to a mammal in need thereof a therapeutically effective amount of a compound of formula (I) as described herein. Autoimmune diseases that may be treated according to the present invention include, but are not limited to, multiple sclerosis (MS), secondary progressive multiple sclerosis (SPMS), psoriasis, rheumatoid arthritis, Crohn's disease, and alopecia areata.

Specific embodiments of the various embodiments described above are defined in more detail below.

Preparation of the Compounds of the Invention

The present invention is further directed to methods of making the compounds of the present invention of Formula (I).

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or aralkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

The use of protecting groups is described in detail in Greene, T. W. and P. G. M. Wuts, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Leaving groups may be added to an intermediate compound to facilitate subsequent reactions. Such leaving groups include, but are not limited to, triflate.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

It is understood that one of ordinary skill in the art would be able to make the compounds of the invention by methods similar to the methods described herein or by methods known to one of ordinary skill in the art. It is also understood that one of ordinary skill in the art would be able to make in a similar manner as described below other compounds of formula (I) not specifically illustrated below by using the appropriate starting components and modifying the parameters of the synthesis as needed. In general, compounds employed as initial starting materials in the synthesis of the compounds of the invention are well known and commercially available, e.g., from Sigma Aldrich, Lancaster Synthesis, Inc., Maybridge, Matrix Scientific, TCI, and Fluorochem USA, etc. To the extent that the compounds employed as initial starting materials are not commercially available, the compounds may be readily synthesized using specific references provided, or by standard procedures commonly employed by those of ordinary skill in the art and/or found in general references text (see, for example, *Comprehensive Organic Transformations*, VCH Publishers Inc., 1989; *Compendium of Organic Synthetic Methods*, Volumes 1-10, 1974-2002, Wiley Interscience; *Advanced Organic Chemistry: Reactions, Mechanisms, and Structure*, 5th edition, Wiley Interscience, 2001; *Advanced Organic Chemistry*, 4th Edition, Part B, Reactions and Synthesis, Kluwer Academic/Plenum Publishers, 2000, etc., and references cited therein).

For example, the following Reaction Scheme 1 (where $Pg^1$, $Pg^2$ and $Pg^3$ are protecting groups) illustrates one method for making compounds of formula (I):

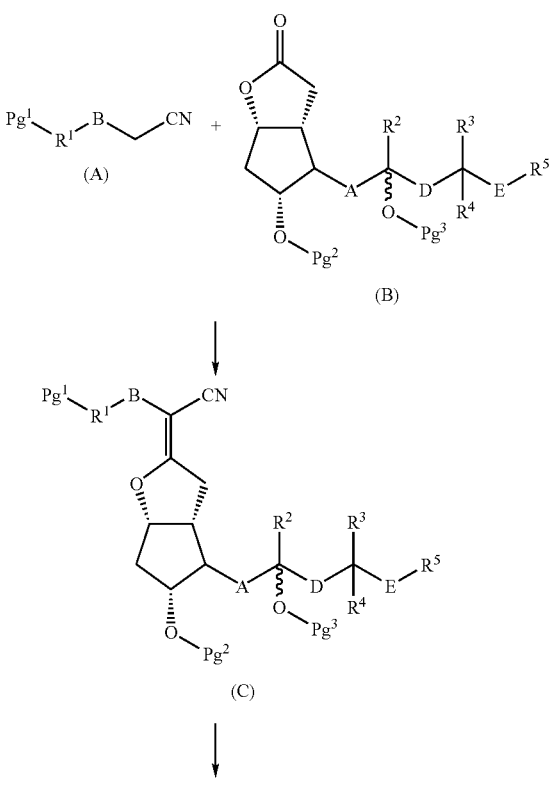

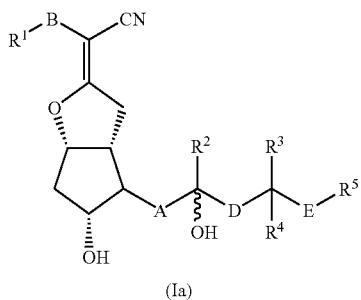

(Ia)

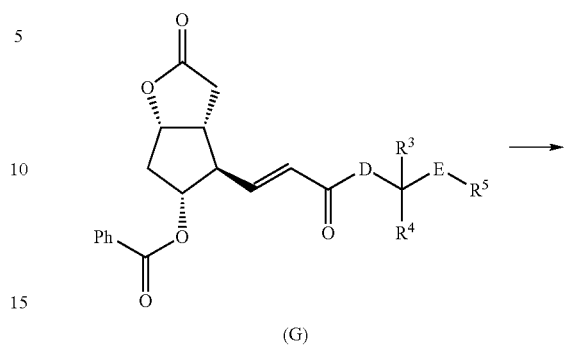

(G)

Generally, a nitrile of formula (A) (where R¹ may have an appended protecting group Pg¹ as necessary) and a cyclopentafuranone of formula (B) are reacted together under appropriate conditions to give a compound of formula (C). The compound of formula (C) is then subjected to appropriate deprotection and hydrolysis conditions to yield a compound of formula (Ia), which is isolated from the reaction mixture by standard isolation techniques.

At the fully deprotected or at the appropriate intermediate stage, the epimers can be separated to give each of the diastereomers as a single compound.

The process outlined in Reaction Scheme 1 is appropriate whether m is zero (not shown in the reaction scheme) or 1 (formula (Ia)).

Compounds of formula (A) and formula (B) are commercially available or are known compounds, or they can be prepared according to methods known to one skilled in the art or by methods disclosed herein. For example, compounds of formula (B) where A is —CH=CH— and Pg³ is a protecting group can be prepared via a Wittig-type reaction. Reaction Scheme 2 illustrates one example of such a synthesis, where R² is hydrogen:

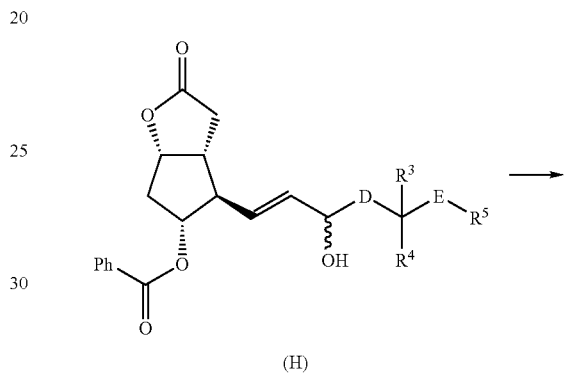

(H)

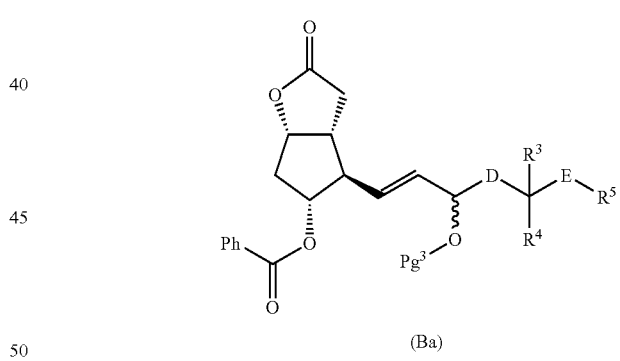

(Ba)

Reaction Scheme 2

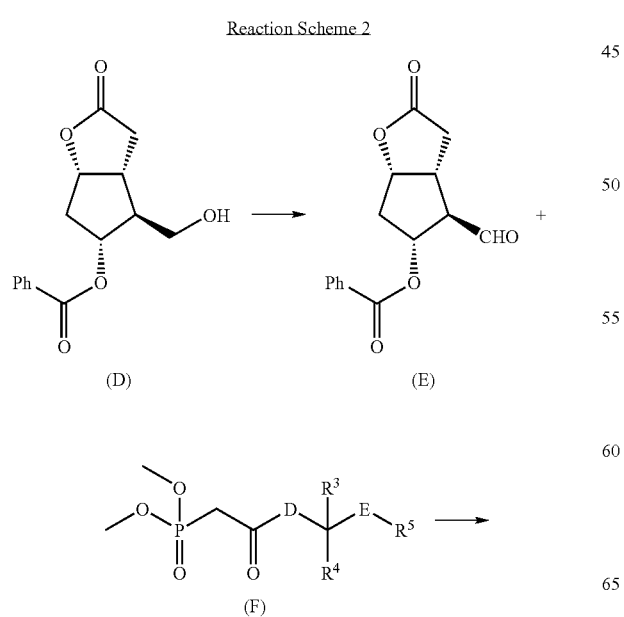

Generally, Corey Lactone (D) is converted to the corresponding carboxaldehyde (E), which is then reacted with a dimethyl phosphonate (F) under appropriate Wittig reaction conditions to give the alkenylcyclopentafuranone (G). Compound (G) is reduced to the corresponding alcohol (H), which is treated with a protecting agent, such as tertbutyldiphenylsilyl chloride, to give the compound of formula (Ba), which is isolated from the reaction mixture by standard isolation techniques.

Compounds of the invention of formula (Ia) where R¹ is tetrazolyl can also be prepared as illustrated in Reaction Scheme 3:

Reaction Scheme 3

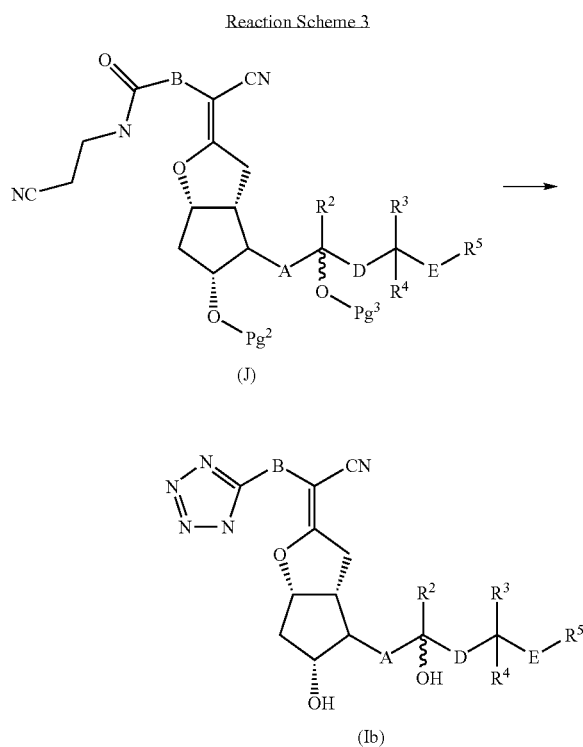

Following the one-step mild conversion of an amide to a tetrazole as described by J. V. Duncia et al. in *J. Org. Chem.* 1991, 56, 2395-2400, the protected amide in compound (J) is converted to a tetrazolyl group, after which the compound is subjected to appropriate deprotection and hydrolysis conditions to yield a compound of formula (Ib), which is isolated from the reaction mixture by standard isolation techniques.

At the fully deprotected or at the appropriate intermediate stage, the epimers can be separated to give each of the diastereomers as a single compound.

The process outlined in Reaction Scheme 3 is appropriate whether m is zero (not shown in the reaction scheme) or 1 (formula (Ib)).

It is understood that other compounds of the invention, not specifically disclosed in the above Reaction Schemes, may be similarly prepared with the appropriate starting materials by one skilled in the art. It is also understood that the compounds prepared above in the foregoing Reaction Schemes may be further treated under, for example, but not limited to, standard esterification conditions, standard acylation conditions, standard alkylation conditions, standard hydrolysis conditions and so forth, to form compounds of the invention not specifically exemplified herein.

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques. It is understood that all polymorphs, amorphous forms, anhydrates, hydrates, solvates and salts of the compounds of the invention are intended to be within the scope of the invention. Furthermore, all compounds of the invention which contain an ester group can be converted to the corresponding acid by methods known to one skilled in the art or by methods described herein.

To prepare the cyclodextrin clathrates of this invention, the compounds of formula (I), as defined above in the Summary of the Invention, can be dissolved in a pharmacologically acceptable solvent, e.g., in an alcohol, preferably ethanol, in a ketone, e.g., acetone or in an ether, e.g., diethyl ether, and mixed with aqueous solutions of α-cyclodextrin, β-cyclodextrin or γ-cyclodextrin, preferably β-cyclodextrin, at 20° C. to 80° C.; or the acids of the compounds of formula (I) as defined above in the Summary of the Invention in the form of the aqueous solutions of their salts (e.g., Na⁻ or K⁻ salts) can be admixed with a cyclodextrin and after solution with the equivalent amount of an acid (e.g., HCl or $H_2SO_4$) to afford the corresponding cyclodextrin clathrate.

At this point or after cooling, the corresponding cyclodextrin clathrates separate in the form of crystals. However, it is also possible to convert oily and also crystalline compounds of formula (I), as defined above in the Summary of the Invention, by rather long stirring (e.g., for 1 hour to 14 days) at ambient temperature, by treatment with an aqueous solution of cyclodextrins, into the corresponding cyclodextrin clathrate form. The clathrates can then be isolated as solid, free-flowing crystals by suctioning off the solvents and drying.

Cyclodextrins used in this invention are commercially available, for example, from Aldrich Chemical Co., or can be prepared by methods known to those skilled in the art. See, for example, Croft, A. P. et al., "Synthesis of Chemically Modified Cyclodextrins", *Tetrahedron* (1983), Vol. 39, No. 9, pp. 1417-1474. Suitable cyclodextrins will include a wide variety of those which produce clathrates of the compounds of formula (I) as set forth above. See, for example, J. E. F. Reynolds (ed.) Martindale, The Extra Pharmacopoeia 28th ed. The Pharmaceutical Press, London 1982, p. 333 and 389-390 and O.-A. Neumueller (ed.), Roempps Chemie-Lexikon, 8. Aufl. Franckh'sche Verlagshandlung, Stuttgart 1981, p. 763-764, 841, 1053-1054.

By selection of suitable amounts of cyclodextrins and water it is possible to obtain the new clathrates in a stoichiometric composition with a reproducible content of effective substance. The clathrates can be used in a dry hygroscopic form or in a water-containing, but less hygroscopic form. Typical molar ratios of cyclodextrin to a compound of formula (I) is 2:1 (cyclodextrin:compound).

Without further elaboration, it is believed that one skilled in the art can, using the preceding description, utilize the present invention to its fullest extent. The following specific Synthetic Preparations (for the preparation of starting materials and intermediates), Synthetic Examples (for the preparation of the compounds of the invention) and the Biological Examples (for the assays used to demonstrate the utility of the compounds of the invention) are provided as a guide to assist in the practice of the invention, and are not intended as a limitation on the scope of the invention. Where one or more NMR's are given for a particular compound, each NMR may represent a single stereoisomer, a non-racemic mixture of stereoisomers or a racemic mixture of the stereoisomers of the compound.

EXAMPLES

Synthetic Preparation 1

Compound of Formula (A)

A solution of adiponitrile (249 g, 2.3 mol) in DMF (400 mL) was stirred as sodium azide (30 g, 460 mmol) and ammonium chloride (24.7 g, 461 mmol) were added. The reaction was heated at 120° C. for 48 h. The reaction was allowed to cool and concentrated. The residue was dissolved in aqueous ether. The aqueous layer was washed with ether (2×). The combined ether layers were concentrated to afford 1H-tetrazole-5-pentanenitrile as a white solid.

A solution of 1H-tetrazole-5-pentanenitrile (30 g, 198 mmol) in a mixture of methylene chloride (200 mL) and triethylamine (30 mL, 218 mmol) was stirred as trityl chloride (61 g, 218 mmol) was added. After 16 h, the reaction was treated with an aqueous solution of sodium bicarbonate and extracted with methylene chloride. The combined organic layers were dried and concentrated. The residue was dissolved in ether and hexane was added. The resulting solid was isolated by filtration to give 1-(triphenylmethyl)-1H-tetrazole-5-pentanenitrile as a white solid.

Synthetic Preparation 2

Compound of Formula (F)

A solution of 2-methylhexanoic acid (20 g, 153 mmol) in methanol (500 mL) was treated with concentrated sulfuric acid (8.0 mL) and heated to 50° C. for 16 h. The reaction was diluted with water and extracted with ether. The combined organic layers were dried and concentrated to afford 20.57 g (93%) of methyl 2-methylhexanoate as a colorless liquid.

A solution of dimethyl methylphosphonate (60 g, 485 mmol) in 600 ml THF was cooled to −78° C. and treated with a 2.5 M solution n-butyl lithium in hexane (194 mL, 485 mmol). After 30 min, the reaction was treated with a solution of methyl 2-methylhexanoate (14 g, 97 mmol) in THF (40 mL). The reaction was stirred for 1 h at −78° C. The reaction was treated with a saturated aqueous ammonium chloride solution (200 mL) and allowed to warm to ambient temperature. The solution was diluted with water and extracted with ether. The combined organic layers were washed with brine, dried, and concentrated. Purification by normal phase chromatography using a gradient of ethyl acetate in hexane gave dimethyl (3-methyl-2-oxoheptyl)phosphonate.

Synthetic Preparation 3

Compound of Formula (E)

A suspension of anhydrous chromium trioxide (20.8 g, 208 mmol) in methylene chloride (400 mL) was stirred and cooled in an ice bath as anhydrous pyridine (32.7 mL, 406 mmol) was added. After 15 min at 0° C., the mixture was allowed to warm to ambient temperature for 2 h. The reaction mixture was cooled to 0° C. and treated with a pre-cooled solution of (3aR,4S,5R,6aS)-5-(benzoyloxy)hexahydro-4-(hydroxymethyl)-2H-cyclopenta[b]furan-2-one (Corey lactone, 9.4 g, 34 mmol) in methylene chloride (400 mL) After 5 min, the reaction was diluted with toluene (240 mL) and filtered. The solid was washed with toluene. The combined filtrate was concentrated to give (3aR,4R,5R,6aS)-5-(benzoyloxy) hexahydro-2-oxo-2H-cyclopenta[b]furan-4-carboxaldehyde. Toluene was added to give about 300 mL of solution.

Synthetic Preparation 4

Compound of Formula (G)

A stirred mixture of a 60% dispersion, in mineral oil, of sodium hydride (2.74 g, 68.7 mmol) in THF (500 mL) was cooled in an ice bath and treated with a solution of dimethyl (3-methyl-2-oxoheptyl)phosphonate (16 g, 67.8 mmol) in 60 mL of THF. The cooling bath was removed and the mixture was stirred at room temperature for 2 h. After cooling to 0° C., the reaction was treated with the solution of (3aR,4R,5R, 6aS)-5-(benzoyloxy)hexahydro-2-oxo-2H-cyclopenta[b]furan-4-carboxaldehyde in toluene from Synthetic Preparation 3, and the mixture was stirred for 40 min at ambient temperature. The reaction mixture was concentrated under reduced pressure and the residue was dissolved in ethyl acetate. The resulting solution was washed with an aqueous 1N solution of HCl, water, and brine, dried, and concentrated. Purification by chromatography on a silica gel column eluting with a gradient of ethyl acetate in hexane to afford (3aR,4R,5R, 6aS)-5-(benzoyloxy)hexahydro-4-[(1E)-4-methyl-3-oxo-1-octenyl]-2H-cyclopenta[b]furan-2-one as an oil.

Synthetic Preparation 5

Compounds of Formulas (H) and (Ba)

A slurry of sodium borohydride (1.8 g, 48 mmol) and cerium chloride (9 g, 24 mmol) in a mixture of methylene chloride (300 mL) and methanol (600 mL) was stirred at room temperature as a solution of (3aR,4R,5R,6aS)-5-(benzoyloxy)hexahydro-4-[(1E)-4-methyl-3-oxo-1-octenyl]-2H-cyclopenta[b]furan-2-one (9.3 g, 24 mmol) in 100 mL of methylene chloride was added. After 30 min, the reaction was treated with water, a saturated ammonium chloride solution, and ethyl acetate. The combined organic layers were dried and concentrated. Purification by normal phase chromatography using a gradient of ethyl acetate in hexane gave (3aR, 4R,5R,6aS)-5-(benzoyloxy)hexahydro-4-[(1E,3S)-3-hydroxy-4-methyl-1-octenyl]-2H-cyclopenta[b]furan-2-one and 3.2 g of the second eluted compound which is the corresponding 3R-isomer, (3aR,4R,5R,6aS)-5-(benzoyloxy) hexahydro-4-[(1E,3R)-3-hydroxy-4-methyl-1-octenyl]-2H-cyclopenta[b]furan-2-one.

A solution of (3aR,4R,5R,6aS)-5-(benzoyloxy)hexahydro-4-[(1E,3S)-3-hydroxy-4-methyl-1-octenyl]-2H-cyclopenta[b]furan-2-one (3.8 g, 9.8 mmol) in DMF (177 mL) was treated with imidazole (1.34 g, 19.66 mmol) and tert-butyldiphenylsilyl chloride (5.1 mL, 19.7 mmol). The reaction mixture was stirred at room temperature for 16 h. The reaction was diluted with water and Ethyl acetate. The combined organic layers were washed with water and brine, dried, concentrated. Purification by normal phase chromatography eluting with a gradient of ethyl acetate in hexane gave (3aR,4R, 5R,6aS)-5-(benzoyloxy)-4-[(1E,3S)-3-[[(1,1-dimethylethyl) diphenylsilyl]oxy]-4-methyl-1-octenyl]hexahydro-2H-cyclopenta[b]furan-2-one as an oil.

Synthetic Example 1

Compound of Formula (I)

A solution of lithium diisopropylamide (13.4 mL, 26.8 mmol, 2M solution) in THF (170 mL) was cooled to −78° C. as a solution of 1-(triphenylmethyl)-1H-tetrazole-5-pentanenitrile (10.55 g, 26.8 mmol) in THF (30 mL) was added slowly. The reaction was allowed to warm to ambient temperature 30 min, before cooling to −78° C. The reaction was stirred as a solution of (3aR,4R,5R,6aS)-5-(benzoyloxy)-4-[(1E,3S)-3-[[(1,1-dimethylethyl)diphenylsilyl]oxy]-4-methyl-1-octenyl]hexahydro-2H-cyclopenta[b]furan-2-one (3.3 g, 5.4 mmol) in THF (50 mL) was added slowly. The reaction was warmed to room temperature and stirred for 16 h. The reaction was treated with an aqueous solution of sodium bicarbonate and extracted with ethyl acetate. The combined organic layers were dried and concentrated. Purification by normal phase chromatography eluting with a gradient of ethyl acetate in hexane afforded α-[(3aR,4R,5R,6aS)-5-(benzoyloxy)-4-[(1E,3S)-3-[[(1,1-dimethylethyl)diphenylsilyl]oxy]-4-methyl-1-octenyl]hexahydro-2-hydroxy-2H-cyclopenta[b]furan-2-yl]-1-(triphenylmethyl)-1H-tetrazole-5-pentanenitrile.

A solution of α-[(3aR,4R,5R,6aS)-5-(benzoyloxy)-4-[(1E,3S)-3-[[(1,1-dimethylethyl)diphenylsilyl]oxy]-4-methyl-1-octenyl]hexahydro-2-hydroxy-2H-cyclopenta[b]furan-2-yl]-1-(triphenylmethyl)-1H-tetrazole-5-pentanenitrile (3.35 g, 3.3 mmol) in THF (366 mL) was stirred as boron trifluoride-diethyl etherate (0.83 mL, 6.6 mmol) was added dropwise. After 30 min, the reaction was treated with an aqueous sodium carbonate solution. The combined organic layers were dried, filtered, and concentrated. Purification by normal phase chromatography eluting with a mixture of ethyl acetate in hexane gave α-[(3aR,4R,5R,6aS)-4-[(1E,3S)-3-[[(1,1-dimethylethyl)diphenylsilyl]oxy]-4-methyl-1-octenyl]hexahydro-5-hydroxy-2H-cyclopenta[b]furan-2-ylidene]-1-(triphenylmethyl)-1H-tetrazole-2E-5-pentanenitrile. In addition, two additional fractions were isolated: (i) a mixture of α-[(3aR,4R,5R,6aS)-5-(benzoyloxy)-4-[(1E,3S)-3-[[(1,1-dimethylethyl)diphenylsilyl]oxy]-4-methyl-1-octenyl]-2E-hexahydro-2H-cyclopenta[b]furan-2-ylidene]-1-(triphenylmethyl)-1H-tetrazole-5-pentanenitrile and α-[(3aR,4R,5R,6aS)-5-(benzoyloxy)-4-[(1E,3S)-3-[[(1,1-dimethylethyl)diphenylsilyl]oxy]-4-methyl-1-octenyl]-2Z-hexahydro-2H-cyclopenta[b]furan-2-ylidene]-1-(triphenylmethyl)-1H-tetrazole-5-pentanenitrile and (ii) the 2Z-isomer, α-[(3aR,4R,5R,6aS)-4-[(1E,3S)-3-[[(1,1-dimethylethyl)diphenylsilyl]oxy]-4-methyl-1-octenyl]hexahydro-5-hydroxy-2H-cyclopenta[b]furan-2-ylidene]-1-(triphenylmethyl)-1H-tetrazole-2Z-5-pentanenitrile.

A solution of α-[(3aR,4R,5R,6aS)-4-[(1E,3S)-3-[[(1,1-dimethylethyl)diphenylsilyl]oxy]-4-methyl-1-octenyl]hexahydro-5-hydroxy-2H-cyclopenta[b]furan-2-ylidene]-1-(triphenylmethyl)-1H-tetrazole-2E-5-pentanenitrile (0.4 g, 0.4 mmol) in methanol (30 mL) was treated with pyridinium p-toluenesulfonate (PPTS, 0.2 g, 0.83 mmol) and stirred at ambient temperature for 16 h. The reaction was concentrated. The residue was dissolved in ethyl acetate and washed with a diluted with a dilute aqueous sodium bicarbonate solution. The combined organic layers were dried, filtered, and concentrated. Purification by normal phase chromatography eluting with a gradient of ethyl acetate in hexane afforded α-[(3aR,4R,5R,6aS)-4-[(1E,3S)-3-[[(1,1-dimethylethyl)diphenylsilyl]oxy]-4-methyl-1-octenyl]hexahydro-5-hydroxy-2H-cyclopenta[b]furan-2-ylidene]-1H-tetrazole-5-2E-pentanenitrile.

A solution of α-[(3aR,4R,5R,6aS)-4-[(1E,3S)-3-[[(1,1-dimethylethyl)diphenylsilyl]oxy]-4-methyl-1-octenyl]hexahydro-5-hydroxy-2H-cyclopenta[b]furan-2-ylidene]-1H-tetrazole-5-2E-pentanenitrile (220 mg, 0.34 mmol) in THF (5 mL) was treated with a 1M solution of tetrabutylammonium fluoride in THF (0.6 mL, 2 mmol). The reaction was stirred at room temperature for 36 h and 16 h at 60° C. for overnight. The reaction was concentrated, dissolved in ethyl acetate, and washed with water. The combined organic layers were dried and concentrated. Purification by normal phase chromatography using a gradient of ethyl acetate in hexane gave α-[(3aR,4R,5R,6aS)-hexahydro-5-hydroxy-4-[(1E,3S)-3-hydroxy-4-methyl-1-octenyl]-2H-cyclopenta[b]furan-2-ylidene]-1H-tetrazole-5-2E-pentanenitrile (Cpd. #1) as a yellow solid; $^1$H NMR (DMSO-d$_6$) δ 5.41 (s, 2H), 4.88 (m, 1H), 3.82 (m, 2H), 3.0 (m, 1H), 2.84 (m, 2H), 2.65 (m, 1H), 2.32 (m, 1H), 2.16 (m, 2H), 1.94 (m, 1H), 1.82 (m, 2H), 1.56 (m, 1H), 1.38 (m, 2H), 1.25 (m, 5H), 0.92 (s, 1H), 0.82 (m, 6H).

Synthetic Example 2

Compound of Formula (I)

One gram of nileprost (5-cyano-16-methylprostacyclin), which is known from U.S. Pat. No. 4,219,479, was dissolved in 16.6 mL DMF, and this solution was treated with 1.74 g imidazole and 1.92 g t-butyldimethylsilyl chloride, with stirring overnight at room temperature (RT). The reaction mixture was diluted with water and then extracted with 100 mL hexane:ether (6:1; 3×). The combined organic phases were washed with 30 mL brine (2×), dried over sodium sulfate, and rotary evaporated. The resulting crude product (2.2 g) was dissolved in 16.6 mL THF and then treated with 16.6 mL water and 1.5 g potassium carbonate, with stirring at RT for 1.5 hr. The reaction mixture was diluted with 100 mL ice watered and 100 mL ether, in an ice bath, and adjusted to pH 4-5 with 10% by vol. H$_2$SO$_4$. The phases were separated and the water phase was extracted with ether. The combined organic phases were washed with 30 mL brine (2×), dried over sodium sulfate, and rotary evaporated. The product was purified in silica gel eluted with 100 mL hexane:ether (3×; 9:1, 8:2, 7:3).

To a solution of 1.477 g of the above carboxylic acid product in 3 mL neat dioxane and 1 mL neat THF was added, at 0° C. under argon, 0.99 mL neat triethylamine and 0.62 mL distilled isobutylchloroformate (in 3 mL dioxane). The reaction was stirred for 2 hr at RT, after which 2.3 g tris-trimethylsilyloxyethylene (see, Wissner, A. et al., *Tetrahedron Letters* 1978, 2749-2752) was added. The reaction was stirred at 90° C. for 4 hr, then cooled to RT, and then treated with a mixture of 5.95 mL dioxane, 2.38 mL water and 1.6 mL acetic acid. The reaction was stirred at 50° C. for 4 hr, then allowed to stand at RT for 13 hr, after which it was concentrated by rotary evaporation, taken up in brine and extracted with methylene chloride. The organic phase was with sodium carbonate (2×) and with brine, dried over sodium sulfate and concentrated. The crude product was purified in silica gel, eluted stepwise with hexane, ether, methanol. Fractions 1 and 2 were repurified in silica gel eluting with methylene chloride and with methylene chloride and methanol. Fractions 15-19 contained the desired hydroxymethylketone product. Protecting groups were then removed and the keto group was reduced to give the final product, 2-[(3aR,4R,5R,6aS)-hexahydro-5-hydroxy-4-[(1E,3S)-3-hydroxy-4-methyl-1-octenyl]-2H-cyclopenta[b]furan-2-ylidene]-6,7-dihydroxy-, (2E)-heptanenitrile (Cpd. #5), $^1$H NMR (CDCl$_3$) d=0.9 (3H), 1.0-2.65 (19H), 2.82-3.05 (2H), 3.47 (1H), 3.63-3.79 (2H), 3.91-4.04 (2H), 4.90 (1H), 5.50 (1H), 5.66 (1H).

Synthetic Example 3

Further Compounds of Formula (I)

Following the general procedures described herein and exemplified in Synthetic Examples 1 and 2, the following compounds, as well as other compounds encompassed within Formula (I) can be synthesized utilizing the appropriate starting materials or intermediates:

α-[(3aR,4R,5R,6aS)-hexahydro-5-hydroxy-4-[(1E,3S)-3-hydroxy-4-methyl-1-octenyl]-2H-cyclopenta[b]furan-2-ylidene]-1H-tetrazole-5-2E-pentanenitrile (Cpd. #2); $^1$H NMR (DMSO-d$_6$) δ 5.41 (s, 2H), 4.83 (m, 1H), 3.75 (m, 2H), 2.82 (m, 3H), 2.55 (m, 1H), 2.32 (m, 1H), 2.13 (m, 2H), 1.94 (m, 1H), 1.82 (m, 2H), 1.63 (m, 1H), 1.38 (m, 2H), 1.18 (m, 5H), 0.92 (s, 1H), 0.82 (m, 3H), 0.74 (m, 3H).

α-[(3aR,4R,5R,6aS)-hexahydro-5-hydroxy-4-[(1 E,3R)-3-hydroxy-4-methyl-1-octenyl]-2H-cyclopenta[b]furan-2-ylidene]-1H-tetrazole-5-2Z-pentanenitrile (Cpd. #3); $^{1}$H NMR (DMSO-d$_{6}$) δ 5.41 (s, 2H), 4.88 (m, 1H), 3.82 (m, 2H), 2.84 (m, 3H), 2.55 (m, 1H), 2.32 (m, 1H), 2.13 (m, 2H), 1.94 (m, 1H), 1.82 (m, 2H), 1.69 (m, 1H), 1.38 (m, 2H), 1.25 (m, 5H), 0.92 (s, 1H), 0.82 (m, 6H).

α-[(3aR,4R,5R,6aS)-hexahydro-5-hydroxy-4-[(1E,3S)-3-hydroxy-1-octenyl]-2H-cyclopenta[b]furan-2-ylidene]-1H-tetrazole-5-pentanenitrile (Cpd. #4); ($^{1}$H NMR (DMSO-d$_{6}$) δ 5.41 (s, 2H), 4.84 (m, 1H), 3.82 (m, 1H), 3.76 (m, 1H), 3.0 (m, 1H), 2.82 (m, 2H), 2.65 (m, 1H), 2.34 (m, 1H), 2.16 (m, 2H), 1.94 (m, 1H), 1.82 (m, 2H), 1.56 (m, 1H), 1.38 (m, 2H), 1.25 (m, 6H), 0.82 (m, 3H).

What is claimed is:

1. A compound of formula (I), or a pharmaceutically acceptable salt thereof:

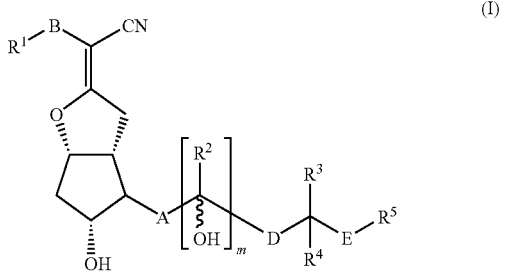

(I)

wherein,
m is zero or one;
$R^{1}$ is tetrazolyl;
B is alkylene of 1-10 carbon atoms;
A is —CH$_{2}$—CH$_{2}$—, —CH═CH—, or —C≡C—;
$R^{2}$ is hydrogen or —CH$_{3}$;
D is a direct bond, alkylene of 1-5 carbon atoms, alkenylene of 2-5 carbon atoms or alkynylene of 2-5 carbon atoms;
$R^{3}$ is hydrogen, hydroxy or alkyl of 1-3 carbon atoms;
$R^{4}$ is hydrogen or alkyl of 1-3 carbon atoms;
or, $R^{3}$ and $R^{4}$ taken together with the carbon to which both $R^{3}$ and $R^{4}$ are attached form a cycloalkylene group of 3-6 carbon atoms;
E is —O—, —S— or a direct bond; and
$R^{5}$ is alkyl, alkenyl, alkynyl, cycloalkyl, heterocyclyl or optionally substituted aryl;
as a single stereoisomer or mixtures of stereoisomers.

2. A compound selected from the following, or a pharmaceutically acceptable salt thereof:
α-[(3aR,4R,5R,6aS)-hexahydro-5-hydroxy-4-[(1E,3S)-3-hydroxy-4-methyl-1-octenyl]-2H-cyclopenta[b]furan-2-ylidene]-1H-tetrazole-5-2E-pentanenitrile;
α-[(3aR,4R,5R,6aS)-hexahydro-5-hydroxy-4-[(1E,3S)-3-hydroxy-4-methyl-1-octenyl]-2H-cyclopenta[b]furan-2-ylidene]-1H-tetrazole-5-2E-pentanenitrile;
α-[(3aR,4R,5R,6aS)-hexahydro-5-hydroxy-4-[(1E,3R)-3-hydroxy-4-methyl-1-octenyl]-2H-cyclopenta[b]furan-2-ylidene]-1H-tetrazole-5-2Z-pentanenitrile; and
α-[(3aR,4R,5R,6aS)-hexahydro-5-hydroxy-4-[(1E,3S)-3-hydroxy-1-octenyl]-2H-cyclopenta[b]furan-2-ylidene]-1H-tetrazole-5-pentanenitrile.

3. A pharmaceutical composition comprising a therapeutically effective amount of a compound according to claim 1 and at least one pharmaceutically acceptable excipient.

4. A method of treating influenza A virus in a patient in need of such treatment, the method comprising administering to the patient an effective amount of a compound according to claim 1.

5. A method according to claim 4 wherein the influenza a virus is influenza A subtype H5N1 virus.

6. A compound according to claim 1 wherein:
m is one;
$R^{1}$ is tetrazolyl;
B is alkylene of 1-10 carbon atoms;
A is —CH═CH—;
$R^{2}$ is hydrogen;
D is a direct bond;
$R^{3}$ is alkyl of 1-3 carbon atoms;
$R^{4}$ is hydrogen;
E is a direct bond; and
$R^{5}$ is alkyl.

7. A pharmaceutical composition according to claim 3 wherein:
m is one;
$R^{1}$ is tetrazolyl;
B is alkylene of 1-10 carbon atoms;
A is —CH═CH—;
$R^{2}$ is hydrogen;
D is a direct bond;
$R^{3}$ is alkyl of 1-3 carbon atoms;
$R^{4}$ is hydrogen;
E is a direct bond; and
$R^{5}$ is alkyl.

8. A pharmaceutical composition according to claim 3 wherein the compound is selected from the following:
α-[(3aR,4R,5R,6aS)-hexahydro-5-hydroxy-4-[(1E,3S)-3-hydroxy-4-methyl-1-octenyl]-2H-cyclopenta[b]furan-2-ylidene]-1H-tetrazole-5-2E-pentanenitrile;
α-[(3aR,4R,5R,6aS)-hexahydro-5-hydroxy-4-[(1E,3S)-3-hydroxy-4-methyl-1-octenyl]-2H-cyclopenta[b]furan-2-ylidene]-1H-tetrazole-5-2E-pentanenitrile;
α-[(3aR,4R,5R,6aS)-hexahydro-5-hydroxy-4-[(1E,3R)-3-hydroxy-4-methyl-1-octenyl]-2H-cyclopenta[b]furan-2-ylidene]-1H-tetrazole-5-2Z-pentanenitrile; and
α-[(3aR,4R,5R,6aS)-hexahydro-5-hydroxy-4-[(1E,3S)-3-hydroxy-1-octenyl]-2H-cyclopenta[b]furan-2-ylidene]-1H-tetrazole-5-pentanenitrile.

9. A method according to claim 4 wherein the compound is selected from the following:
α-[(3aR,4R,5R,6aS)-hexahydro-5-hydroxy-4-[(1E,3S)-3-hydroxy-4-methyl-1-octenyl]-2H-cyclopenta[b]furan-2-ylidene]-1H-tetrazole-5-2E-pentanenitrile;
α-[(3aR,4R,5R,6aS)-hexahydro-5-hydroxy-4-[(1E,3S)-3-hydroxy-4-methyl-1-octenyl]-2H-cyclopenta[b]furan-2-ylidene]-1H-tetrazole-5-2E-pentanenitrile;
α-[(3aR,4R,5R,6aS)-hexahydro-5-hydroxy-4-[(1E,3R)-3-hydroxy-4-methyl-1-octenyl]-2H-cyclopenta[b]furan-2-ylidene]-1H-tetrazole-5-2Z-pentanenitrile; and
α-[(3aR,4R,5R,6aS)-hexahydro-5-hydroxy-4-[(1E,3S)-3-hydroxy-1-octenyl]-2H-cyclopenta[b]furan-2-ylidene]-1H-tetrazole-5-pentanenitrile.

10. A method according to claim 5 wherein the compound is selected from the following:
α-[(3aR,4R,5R,6aS)-hexahydro-5-hydroxy-4-[(1E,3S)-3-hydroxy-4-methyl-1-octenyl]-2H-cyclopenta[b]furan-2-ylidene]-1H-tetrazole-5-2E-pentanenitrile;

α-[(3aR,4R,5R,6aS)-hexahydro-5-hydroxy-4-[(1E,3S)-3-hydroxy-4-methyl-1-octenyl]-2H-cyclopenta[b]furan-2-ylidene]-1H-tetrazole-5-2E-pentanenitrile;

α-[(3aR,4R,5R,6aS)-hexahydro-5-hydroxy-4-[(1E,3R)-3-hydroxy-4-methyl-1-octenyl]-2H-cyclopenta[b]furan-2-ylidene]-1H-tetrazole-5-2Z-pentanenitrile; and α-[(3aR,4R,5R,6aS)-hexahydro-5-hydroxy-4-[(1E,3S)-3-hydroxy-1-octenyl]-2H-cyclopenta[b]furan-2-ylidene]-1H-tetrazole-5-pentanenitrile.

* * * * *